United States Patent
Bertrand et al.

(10) Patent No.: US 9,916,615 B2
(45) Date of Patent: Mar. 13, 2018

(54) ORDER HISTORY ANALYZING SYSTEMS AND METHODS

(75) Inventors: Mike Bertrand, Upton, MA (US);
Rachel O'Reilly, Newton, MA (US);
Paul W. Brient, Wayland, MA (US);
Fei Wang, Newton, MA (US)

(73) Assignee: PATIENTKEEPER, INC., Waltham, MA (US)

( * ) Notice: Subject to any disclaimer, the term of this patent is extended or adjusted under 35 U.S.C. 154(b) by 625 days.

(21) Appl. No.: 13/398,650

(22) Filed: Feb. 16, 2012

(65) Prior Publication Data

US 2013/0218580 A1   Aug. 22, 2013

(51) Int. Cl.
*G06Q 30/06* (2012.01)
*G06F 19/00* (2018.01)
*G06Q 30/02* (2012.01)
*G06Q 50/22* (2018.01)

(52) U.S. Cl.
CPC ..... *G06Q 30/0633* (2013.01); *G06F 19/3456* (2013.01); *G06Q 30/0255* (2013.01); *G06F 19/322* (2013.01); *G06Q 50/22* (2013.01)

(58) Field of Classification Search
CPC .... G06Q 50/22; G06F 19/322; G06F 19/3456
USPC ....................................................... 705/2–3
See application file for complete search history.

(56) References Cited

U.S. PATENT DOCUMENTS

| | | | | |
|---|---|---|---|---|
| 5,758,095 A | * | 5/1998 | Albaum ................ | G06F 19/322 705/2 |
| 2002/0042726 A1 | * | 4/2002 | Mayaud ................ | G06F 19/322 705/2 |
| 2002/0072934 A1 | * | 6/2002 | Ross ..................... | G06F 19/322 705/3 |
| 2002/0091576 A1 | * | 7/2002 | Giordano, III ....... | G06Q 10/087 705/2 |
| 2004/0006490 A1 | * | 1/2004 | Gingrich ............... | G06F 19/328 705/2 |

* cited by examiner

*Primary Examiner* — Joy Chng
(74) *Attorney, Agent, or Firm* — Kilpatrick Townsend & Stockton, LLP

(57) ABSTRACT

A computer-readable medium storing computer-executable instructions for: (1) receiving information regarding a plurality of past orders placed by health care providers at a particular health care facility; (2) using the information regarding the plurality of past orders to determine a set of most commonly prescribed orders for the health care facility; (3) converting the set of most commonly prescribed orders from a first format to a second format; (4) displaying the set of most commonly prescribed orders to a user in the second format; and (5) allowing the user to place a new order by selecting one of the most commonly prescribed orders.

20 Claims, 7 Drawing Sheets

| Modification Orders | | | | |
|---|---|---|---|---|
| Medication (26) | Dose | SIG | Order Start | Order Stop | Last Admin |
| MAGNESIUM HYDROXIDE | 30 MG | PO ONCE DAILY PRN | 02/09/12 02:30pm | 03/10/12 02:31pm | |
| BACITRACIN OINT | SM AMT | TOP BID-PRN | 02/09/12 02:30pm | 02/22/12 02:31pm | |
| DULCOLAX (BISACODYL) | 10 MG | PR Q72H (PRN) | 02/09/12 02:30pm | 03/10/12 02:31pm | |
| MAALOX (ALUM & MAG SUSP) | 10 MG | PR Q72H (PRN) | 02/09/12 02:30pm | 03/10/12 02:31pm | |
| LIDOCAINE 1% SOL | 2.1 ML | IM.PRN FOR ROCPHIN | 02/09/12 02:30pm | 03/10/12 02:31pm | |
| ROBITUSSIN 100MG/5ML SYP | 200 MG | PO Q4H (PRN) | 02/09/12 02:30pm | 02/10/12 02:31pm | |
| PNEUMOCOCCAL VACCINE | 0.5 ML | IM PER PROTOOCL (PRN) | 02/09/12 02:30pm | 03/10/12 02:31pm | |
| DUONEB (ALB/IPRAT) | 0.5 MG | IN Q4H (PRN) | 02/09/12 02:30pm | 03/10/12 02:31pm | |
| LEVAQUIN (LEVOFLOXACIN) | 500 MG | PO 6AM | 02/09/12 02:30pm | 02/11/12 60:01pm | 02/09/12 02:56PM |

401

ORDER HISTORY ANALYZING SYSTEMS AND METHODS

BACKGROUND

Health care facilities and physicians desire systems for efficiently and accurately creating orders for patients. Accordingly, there is a need for improved systems for allowing users to create orders accurately and efficiently.

SUMMARY OF VARIOUS EMBODIMENTS

A computer-readable medium, according to particular embodiments, stores computer-executable instructions for: (1) receiving information regarding a plurality of past orders placed by health care providers at a particular health care facility; (2) using the plurality of past orders to determine a set of most commonly prescribed orders for the health care facility; (3) displaying the set of most commonly prescribed orders to a user; and (4) allowing the user to place a new order by selecting one of the most commonly prescribed orders.

A computer-readable medium, according to particular embodiments, stores computer-executable instructions for: (1) receiving information regarding a plurality of past orders placed by a physician; (2) using the plurality of past orders to determine a set of most commonly prescribed orders for the physician; (3) displaying the set of most commonly prescribed orders to a user; and (4) allowing the user to place a new order by selecting one of the most commonly prescribed orders.

BRIEF DESCRIPTION OF THE DRAWINGS

Figure 1:
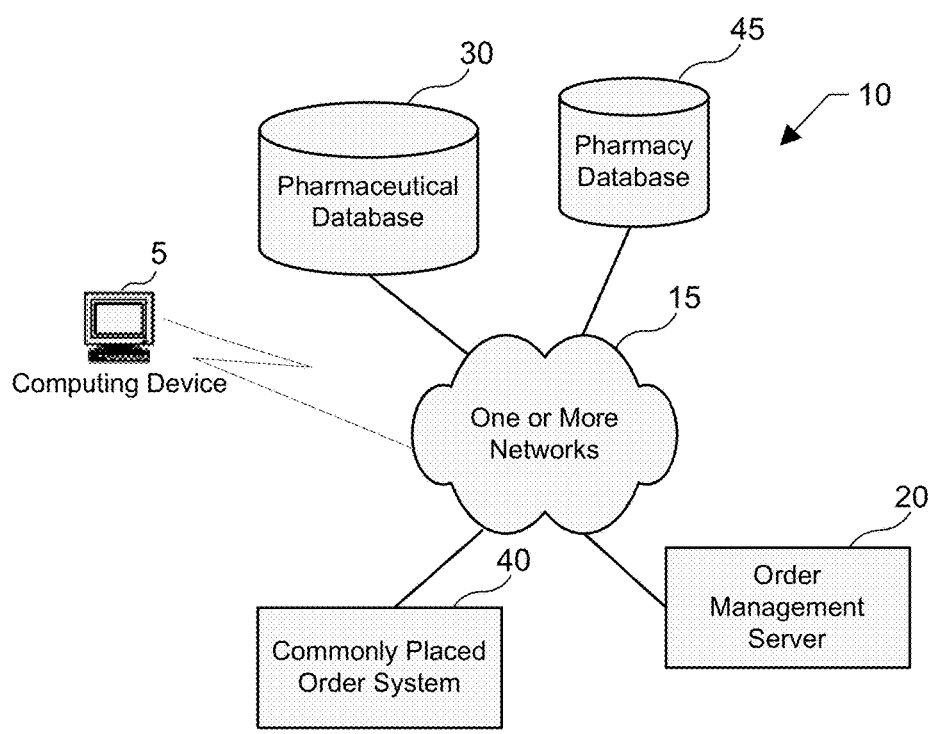

Having thus described various embodiments in general terms, reference will now be made to the accompanying drawings, which are not necessarily drawn to scale, and wherein:

FIG. 1 is a block diagram of an Order Management System according to one embodiment.

Figure 2:
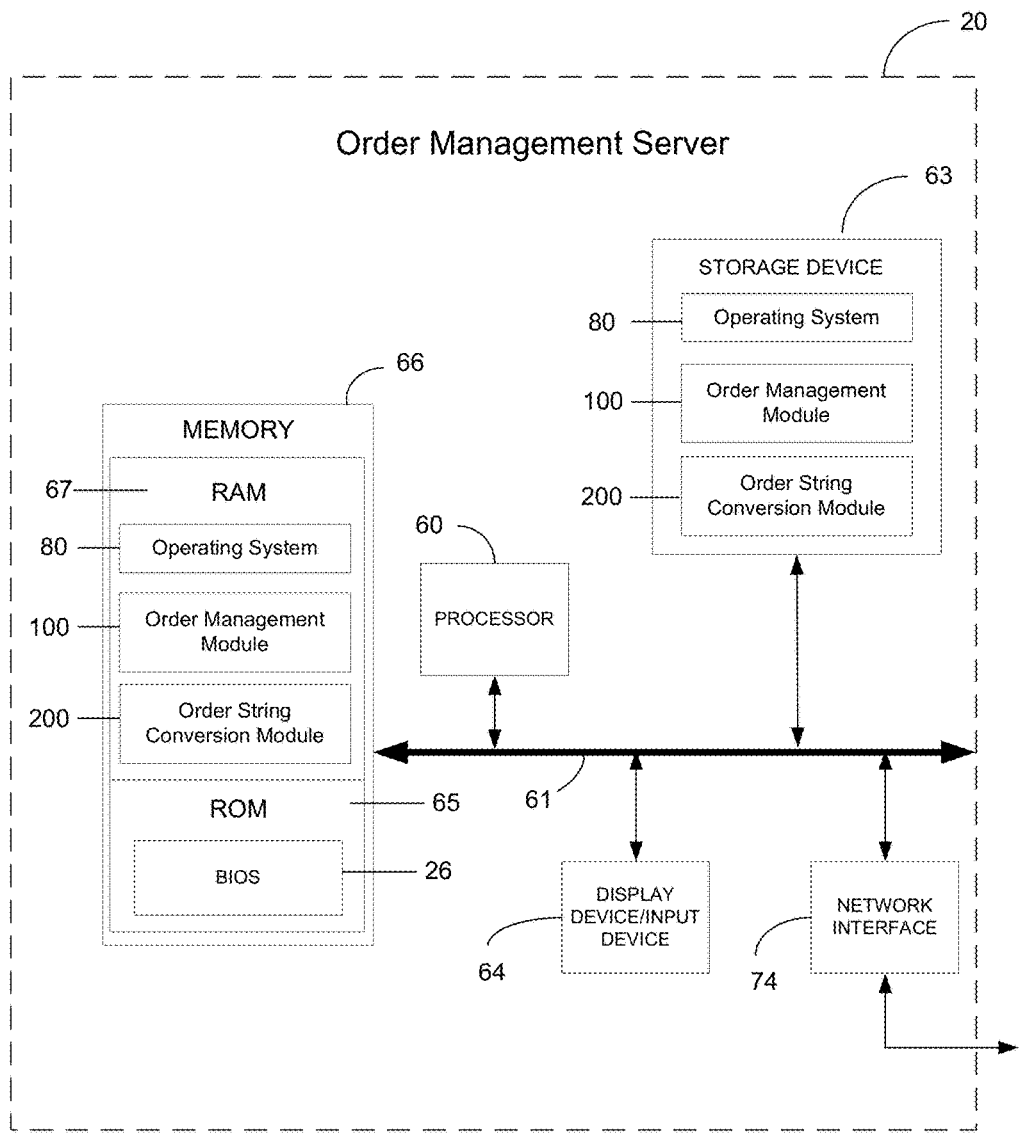

FIG. 2 is a block diagram of the Order Management Server of FIG. 1.

Figure 3:
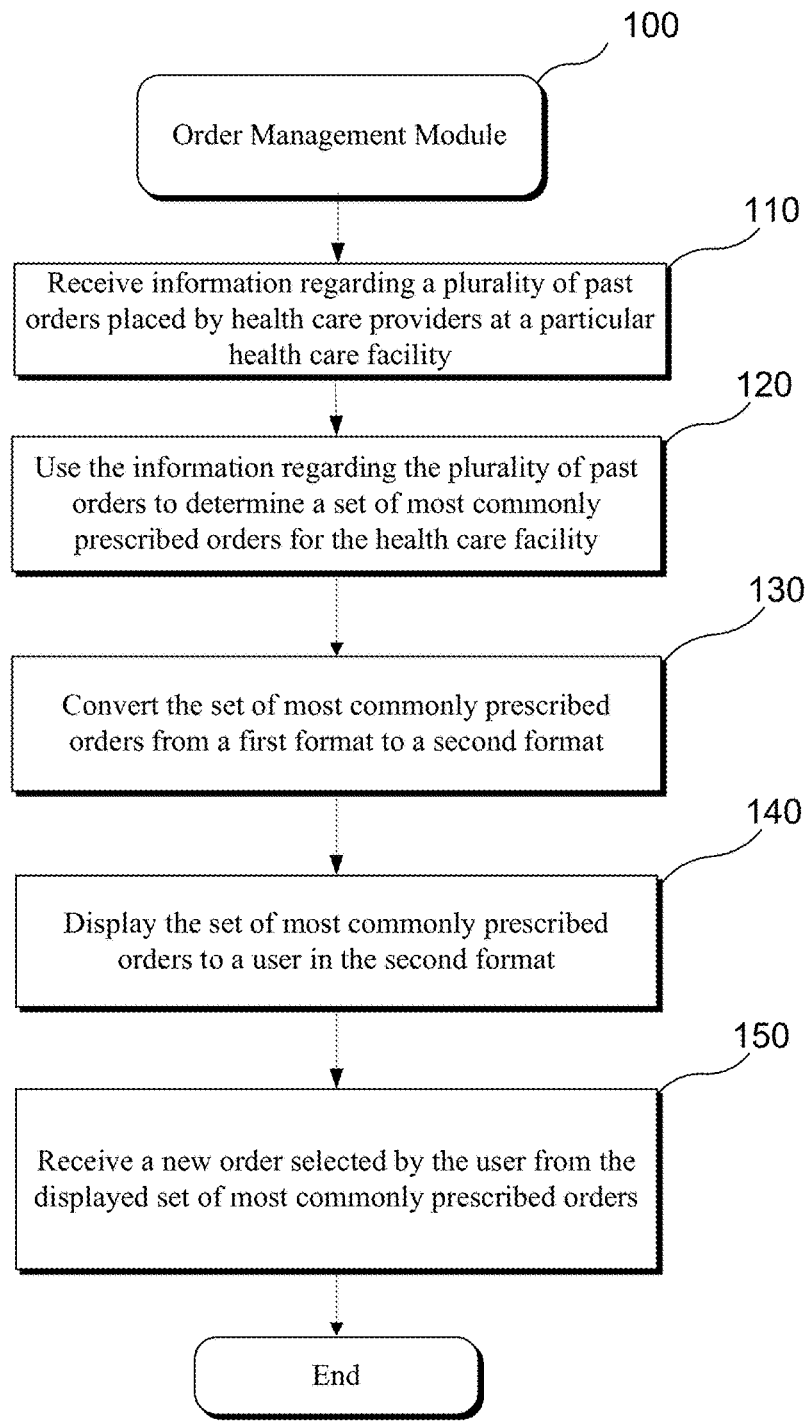

FIG. 3 is a flowchart of steps executed by an Order Management Module according to a particular embodiment.

Figure 4:
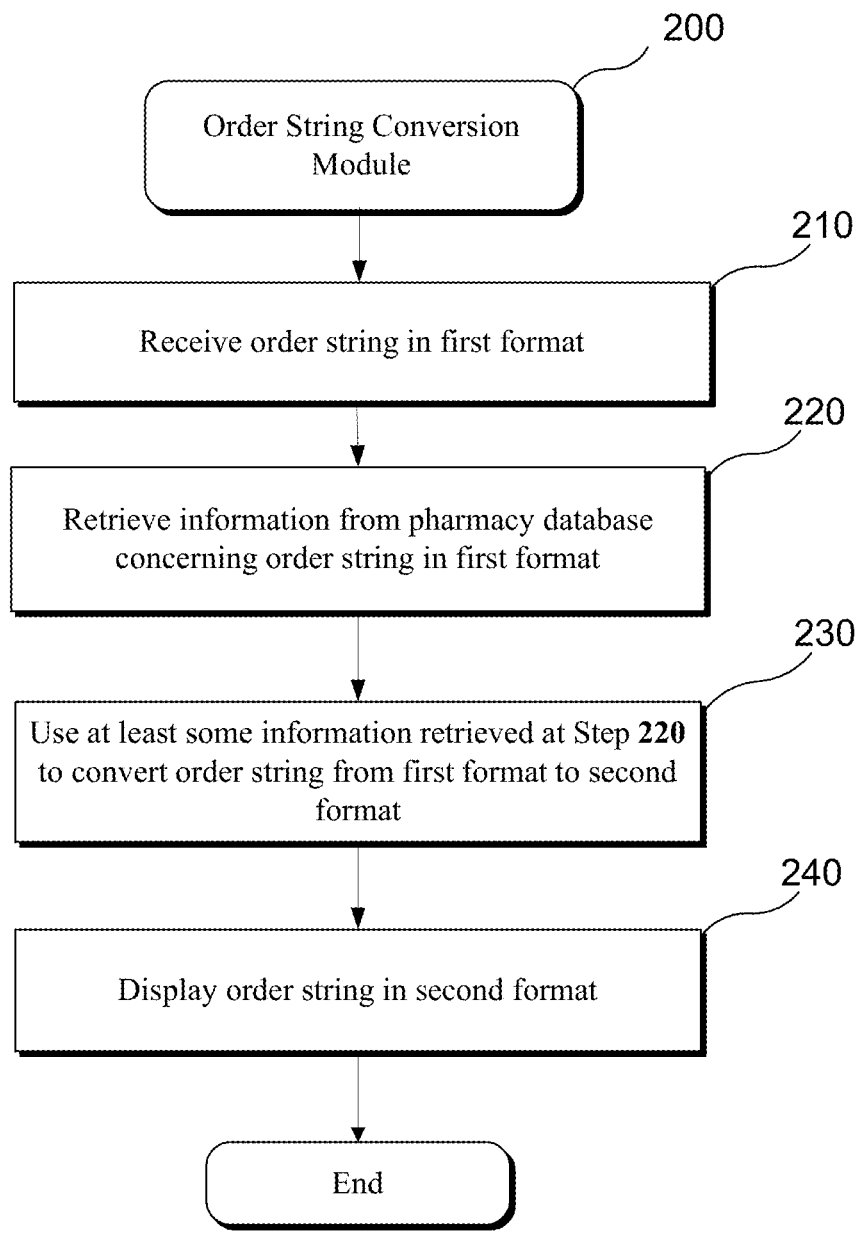

FIG. 4 is a flowchart of steps executed by an Order String Conversion Module according to a particular embodiment.

Figure 5:
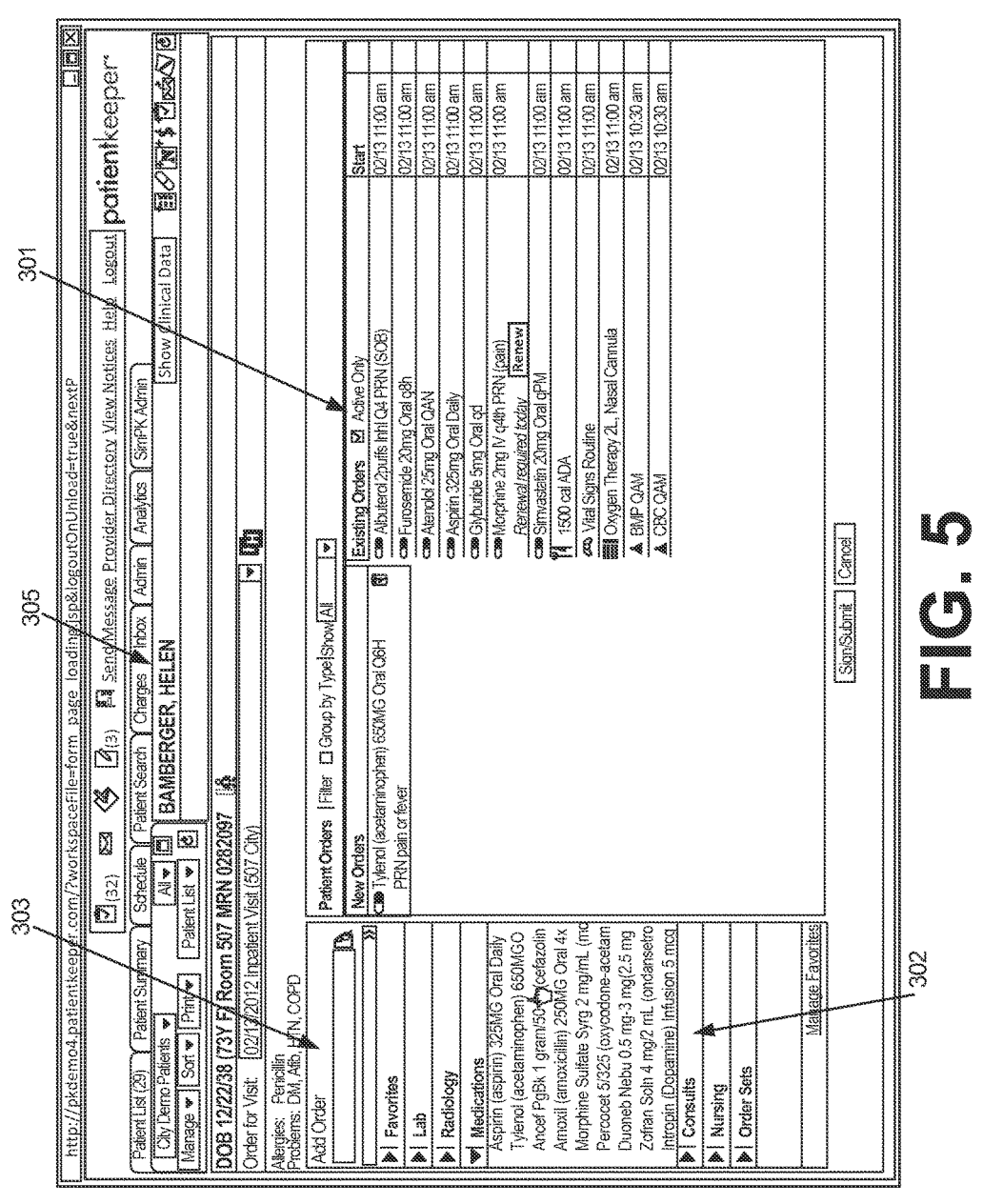
Figure 6:
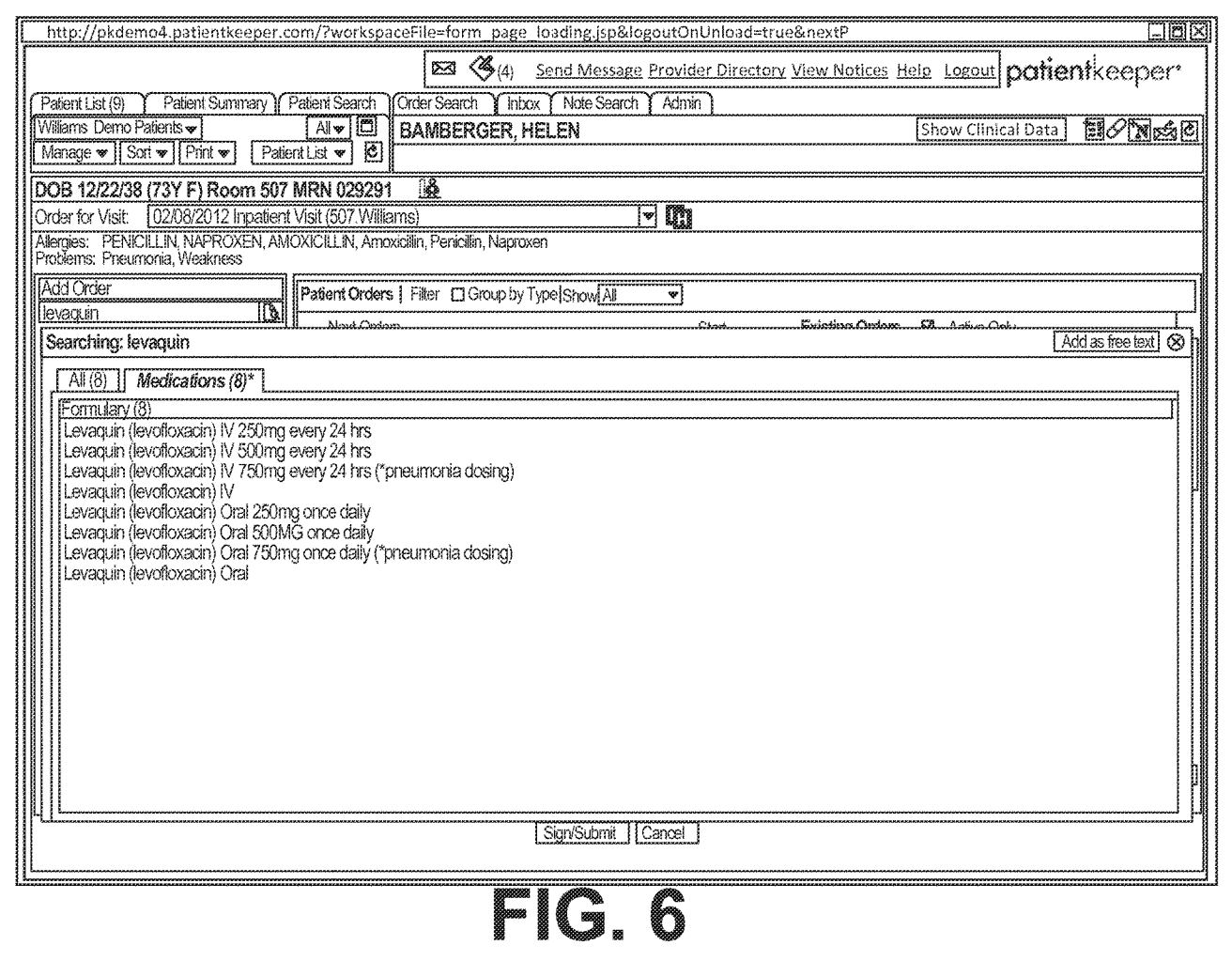

FIGS. 5-7 are screen shots of exemplary user interfaces for an Order Management System according to various embodiments.

DETAILED DESCRIPTION OF VARIOUS EMBODIMENTS

Various embodiments now will be described more fully hereinafter with reference to the accompanying drawings. It should be understood that the invention may be embodied in many different forms and should not be construed as limited to the embodiments set forth herein. Rather, these embodiments are provided so that this disclosure will be thorough and complete, and will fully convey the scope of the invention to those skilled in the art. Like numbers refer to like elements throughout.

Overview

Health care professionals place thousands of orders every year for prescriptions, which may include, for example, a specific combination of a medication, a dosage, and a route (e.g., by mouth, eye drop, intravenously, etc.). Because of the vast number of prescription drugs and potential dosage amounts and delivery methods, the catalog of potential prescription order combinations may be vast. When placing an order for a prescription drug via a computerized ordering system (e.g., via a drop down menu), health care professionals may have trouble sifting through the potentially millions of combinations of medications, dosages, and delivery routes. Physicians may prefer to write out orders on paper than scroll through pages of medications in computerized ordering software in order to place a desired prescription order.

Various embodiments of an Order Management System may allow particular health care facilities or health care professionals to select from commonly prescribed medications relating to their particular practice area. Such health care facilities and health care professionals may be able to utilize a computerized ordering system that allows users to choose an order from a list of commonly placed orders, rather than wading through an endless list of all possible orders.

In particular embodiments, a mobile computing device (such as a laptop computer, tablet computer, smart phone, or similar device) can be used to compile information about past orders placed, for example, at a particular health care facility or by a particular physician. In various embodiments, the system may then display the most commonly placed orders on the mobile computing device. A health care professional may then place a prescription order by choosing from the list of most commonly placed orders. In various embodiments, the use of a computerized ordering system by health care professionals may help physicians create more accurate orders.

As may be appreciated by one skilled in the relevant field, pharmacists, when filling prescriptions, may need to translate a physician's order string into a format that the pharmacist can use to fulfill the prescription and that can be easily understood by a patient when reading a prescription's labeling. In particular embodiments, an order history analyzing system may be adapted to translate past order information from a first, pharmacy format to a second, physician format before displaying common orders to the prescribing physician.

Exemplary Technical Platforms

As will be appreciated by one skilled in the relevant field, the present invention may be, for example, embodied as a computer system, a method, or a computer program product. Accordingly, various embodiments may take the form of an entirely hardware embodiment, an entirely software embodiment, or an embodiment combining software and hardware aspects. Furthermore, particular embodiments may take the form of a computer program product stored on a computer-readable storage medium having computer-readable instructions (e.g., software) embodied in the storage medium. Various embodiments may take the form of web-implemented computer software. Any suitable computer-readable storage medium may be utilized including, for example, hard disks, compact disks, DVDs, optical storage devices, and/or magnetic storage devices.

Various embodiments are described below with reference to block diagrams and flowchart illustrations of methods, apparatuses (e.g., systems) and computer program products. It should be understood that each block of the block diagrams and flowchart illustrations, and combinations of blocks in the block diagrams and flowchart illustrations, respectively, can be implemented by a computer executing computer program instructions. These computer program instructions may be loaded onto a general purpose computer, special purpose computer, or other programmable data processing apparatus to produce a machine, such that the instructions which execute on the computer or other programmable data processing apparatus create means for implementing the functions specified in the flowchart block or blocks.

These computer program instructions may also be stored in a computer-readable memory that can direct a computer or other programmable data processing apparatus to function in a particular manner such that the instructions stored in the computer-readable memory produce an article of manufacture that is configured for implementing the function specified in the flowchart block or blocks. The computer program instructions may also be loaded onto a computer or other programmable data processing apparatus to cause a series of operational steps to be performed on the computer or other programmable apparatus to produce a computer implemented process such that the instructions that execute on the computer or other programmable apparatus provide steps for implementing the functions specified in the flowchart block or blocks.

Accordingly, blocks of the block diagrams and flowchart illustrations support combinations of mechanisms for performing the specified functions, combinations of steps for performing the specified functions, and program instructions for performing the specified functions. It should also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and other hardware executing appropriate computer instructions.

Exemplary System Architecture

FIG. 1 shows a block diagram of an Order Management System 10 according to a particular embodiment. As may be understood from this figure, the Order Management System 10 includes at least one computing device 5 (which may include, for example, a tablet, computer, smart phone, laptop, or other suitable computing device), one or more computer networks 15, an Order Management Server 20, a Pharmaceutical Database 30, a Commonly Placed Order System 40, and a Pharmacy Database 45. The one or more computer networks 15 facilitate communication between the computing device 5, Order Management Server 20, Pharmaceutical Database 30, Commonly Placed Order System 40, and Pharmacy Database 45. These one or more computer networks 15 may include any of a variety of types of computer networks such as the Internet, a private intranet, a public switch telephone network (PSTN), or any other type of network known in the art. In certain variations of the embodiment shown in FIG. 1, both the communication link between the computing device 5, Order Management Server 20, Pharmaceutical Database 30, Commonly Placed Order System 40, and Pharmacy Database 45 are implemented via the Internet using Internet protocol (IP). The communication link between the Order Management Server 20 and the Pharmacy Database 45 may be, for example, implemented via a Local Area Network (LAN).

FIG. 2 shows a block diagram of an exemplary embodiment of the Order Management Server 20 of FIG. 1. The Order Management Server 20 includes a processor 60 that communicates with other elements within the Order Management Server 20 via a system interface or bus 61. Also included in the Order Management Server 20 is a display device/input device 64 for receiving and displaying data. This display device/input device 64 may be, for example, a keyboard, voice recognition, or pointing device that is used in combination with a monitor. The Order Management Server 20 further includes memory 66, which preferably includes both read only memory (ROM) 65 and random access memory (RAM) 67. The server's ROM 65 is used to store a basic input/output system 26 (BIOS) that contains the basic routines that help to transfer information between elements within the Order Management Server 20.

In addition, the Order Management Server 20 includes at least one storage device 63, such as a hard disk drive, a floppy disk drive, a CD Rom drive, or optical disk drive, for storing information on various computer-readable media, such as a hard disk, a removable magnetic disk, or a CD-ROM disk. As will be appreciated by one of ordinary skill in the relevant field, each of these storage devices 63 is connected to the system bus 61 by an appropriate interface. The storage devices 63 and their associated computer-readable media provide nonvolatile storage for the Order Management Server 20. It is important to note that the computer-readable media described above could be replaced by any other type of computer-readable media known in the relevant field. Such media include, for example, magnetic cassettes, flash memory cards, digital video disks, and Bernoulli cartridges.

A number of program modules may be stored by the various storage devices and within RAM 67. Such program modules include an operating system 80, an Order Management Module 100, and an Order String Conversion Module 200. The Order Management Module 100 and Order String Conversion Module 200 control certain aspects of the operation of the Order Management Server 20, as is described in more detail below, with the assistance of the processor 60 and an operating system 80.

Also located within the Order Management Server 20 is a network interface 74 for interfacing and communicating with other elements of a computer network. It will be appreciated by one of ordinary skill in the art that one or more of the Order Management Server 20 components may be located geographically remotely from other Order Management Server 20 components. Furthermore, one or more of the components may be combined, and additional components performing functions described herein may be included in the Order Management Server 20.

Exemplary System Modules

As noted above, various aspects of the system's functionality may be executed by certain system modules, including the system's Order Management Module 100 and Order String Conversion Module 200. These modules are described in more detail below.

Order Management Module

FIG. 3 is a flow chart of an exemplary Order Management Module 100. As may be understood from FIG. 3, certain embodiments of an Order Management Module 100 are configured to provide a user (e.g., a health care provider such as a physician) with a set of most common orders for prescriptions from which to select a new prescription order. For example, if a physician needs to create an order for a particular drug, the physician may simply select the drug from a list of most commonly ordered prescriptions rather than having to write a prescription by hand or search through a large database for the particular drug.

Beginning at Step 110, the system receives information regarding a plurality of past orders placed by health care providers at a particular health care facility (e.g., during a predefined time period). These past orders may include, for example, orders made at a pharmacy associated with the particular health care facility during a specified period (e.g., the last six months). In particular embodiments, the health care provider may include all of the health care professionals in a hospital. In other embodiments, a health care provider may be an individual health care professional, such as a physician or surgeon. In various embodiments, the information regarding the plurality of past orders may comprise, for each order, the drug entity to be taken by a patient, a dosage of the drug entity to be taken by the patient, and a route of administration for the drug entity (e.g., orally, intravenously, etc.).

The system then uses the information regarding the plurality of past orders, at Step 120, to determine a set of most commonly prescribed orders for the health care facility over the predefined time period. The set of most commonly prescribed orders may include, for example, information about the name of a particular prescription drug, the dosage of the particular drug, the concentration of the particular drug, or any other pertinent information related to the ordering of prescription drugs. In various embodiments, the set of most commonly prescribed drugs may be specific to a particular health care professional, or may be based at least in part on all ordered prescriptions for an entire health care facility (e.g., historically in the predefined time period). In various embodiments, the set of most commonly prescribed orders may include the top ten ordered prescriptions; in other embodiments, the set of most commonly prescribed orders may include a top one hundred list of ordered prescriptions, or any other suitable number of most common orders.

In various embodiments, the set of most commonly prescribed orders may be determined by counting the total number of a particular order from a pharmacy database of past orders. For example, the system may count the total number of each particular order and compare the totals for each order against one another to determine which the most commonly prescribed orders are. In other embodiments, the system may count the number of orders and determine if the total number of a particular order exceeds a predefined threshold value. The predefined threshold value may, for example, be used to determine whether a particular order is common enough to warrant consideration as a most common order. The system may then compare the orders that exceed the predefined threshold value to determine which of the orders that exceed the predefined threshold are the most common.

The system then converts, at Step 130, the set of most commonly prescribed orders from a first format to a second format. In particular embodiments, the first format may be a pharmacy order format, and the second format may be a physician order format. In various embodiments, the physician order format may be a format in which a physician would typically create an order. In particular embodiments, conversion of the set of most commonly prescribed orders at Step 130 may be optional.

The system then displays, at Step 140, the set of most commonly prescribed orders to a user in the second format. The user of the system may include any health care or other professional that is entering an order for a prescription drug. The system may display the most commonly prescribed orders, for example, on a smart phone, tablet, laptop, or any other suitable computing device.

The system then receives, at Step 150, a new order selected by the user from the set of most commonly prescribed orders displayed to the user at Step 140. The system may receive the order, for example, via the user's input on a touch screen display (e.g., the touch screen display of a smart phone or tablet computer), or by any other suitable method such as a using a mouse associated with a desktop computer.

Order String Conversion Module

FIG. 4 is a flow chart of an exemplary Order String Conversion Module 200. As may be understood from FIG. 4, certain embodiments of an Order String Conversion Module 200 are configured to convert an order from a first format to a second format. In various embodiments, the first format may be a pharmacy order format and the second format may be a physician order format. For example, an order in a pharmacy format may be limited by what medications are available in stock in a pharmacy. For example, a pharmacy may only have certain medications available in certain forms (e.g., pill form) or in certain doses (e.g., 50 mg). An exemplary pharmacy order may include a requirement that a patient take two 325 mg Acetaminophen pills every four hours. The same order in a physician format may simply require the patient to take 650 mg of Acetaminophen every four hours.

When executing this module, the system begins, at Step 210, by receiving an order string in a first format such as a pharmacy order format. In various embodiments, the order string in the first format may be an order string from a previously placed order with a particular pharmacy. In particular embodiments, an order string in the pharmacy order format may include the name of a medication, a dose, and a route of administration. In various embodiments, an order string in the pharmacy order format may include a brand name of a medication such as Zoloft. The first string in the pharmacy order format may include instructions on when to take the medication (e.g., Q6H, meaning take every six hours). An exemplary order string in a pharmacy format for a prescription for a patient with high cholesterol may be: "Zocor 5 mg. Sig: ii po qhs", which calls for a prescription of Zocor with a 5 mg dose with instructions to take two pills, by mouth, at bedtime.

The system then, at Step 220, retrieves information relating to the order string in the pharmacy order format from a pharmaceutical database. The information may include, for example, National Drug Code (NDC) information for the order string, and the pharmaceutical database may include any suitable database containing pharmaceutical data such as First Databank. Continuing the high cholesterol example above, the system, at Step 220, may find information in the pharmacy database including information that the generic name for Zocor is Simvastatin.

The system then converts the order string, at Step 230, from the first, pharmacy format to a second format. In various embodiments, the second format may be a physician format that may be used by physicians when writing prescriptions. In particular embodiments, the system may use information retrieved at Step 220 to convert the order string from the first order format to the second order format. For example, in the high cholesterol example, the physician order format for the Zocor prescription may include an order string such as "Simvastatin 10 mg. Oral at bedtime", which calls for a prescription of the generic drug Simvastatin with a 10 mg dose with instructions to take by mouth, at bedtime. Although this string differs from the pharmacy string above, this physician string would be properly filled by the above order string for Zocor in the pharmacy order format. The conversion from the pharmacy order format to the physician order format in this example may include the following:

1. Converting the brand name into the generic drug name which was determined at Step 220 using the pharmaceutical database (e.g., converting Zocor to Simvastatin);
2. Converting the dosage and amount of the drug into a total dosage (e.g., converting a direction to take two 5 mg pills to a 10 mg dose);
3. Converting the pharmacy string for the delivery route to a physician string (e.g., converting "po" to "oral"); and
4. Converting the pharmacy string for a time to take the medication to a physician string (e.g., converting "qhs" to "at bedtime").

The order strings in this example may differ due to availability (e.g., the only form of Simvastatin the pharmacy had when filling the prescription was Zocor or the only Simvastatin pills the pharmacy had available were in 5 mg doses). A physician, when creating a prescription, may not be aware of a particular pharmacy's availability.

The system then displays, at Step 240, the order string in the second format. The system may display the second string, for example, on a screen associated with a computing device such as a smart phone, laptop, tablet, or desktop computer. Displaying the order string in the second format may allow an ordering physician to select an order string based on the format in which the ordering physician generally writes prescriptions.

Exemplary User Experience

FIG. 5 shows an exemplary user interface of an Order Management System according to a particular embodiment. As shown in this figure, the user interface may include information about a patient for which the user desires to place an order. The information about the patient may include, for example, the patient's name 305, and other information about the patient such as allergies. Via the user interface, the user (e.g., a physician or other health care professional) may view a list of existing orders 301 that the user has placed. In various embodiments, the list of existing orders 301 may include information about when the order was placed, what medication or drug was ordered, the dosage ordered, and any other information relevant to the order.

As may be understood form FIG. 5, the user may select from various menus of most common orders 302 when placing an order. The menus of most common orders may include, for example, the most common orders from the Laboratory, Radiology, orders for Medications, Consultation orders, Nursing orders, or any other types of orders that a user may need to place. FIG. 5 shows the user interface with the most common Medication order menu expanded showing nine most common orders. As may be understood from this figure, the user may simply select the medication that they wish to order from the list of most common orders (e.g., using a pointer device such as a mouse) to create a new order for the medication. When a user wishes to create an order for a medication that is not on the list of most common orders, the user may search for orders that include, for example, the name of the medication by using a search box 303.

FIG. 6 depicts the search results after a user has entered a search for orders including the medication Levaquin. As may be understood from FIG. 6, the search results may include the medication in various doses, delivery methods (e.g., IV or orally), and delivery times (e.g., every 24 hours) for selection by the user. In various embodiments, the user interface may display medications in a physician order format as shown in FIG. 6.

FIG. 7 depicts a user interface listing medication orders in a pharmacy format. The user interface shown in this figure may represent the interface that a pharmacist sees listing all of the orders placed by various health care professionals in a hospital. The order for "Levaquin 500 mg: PO 6AM" 401 in FIG. 7, for example, may represent the pharmacy order of the physician order for "Levaquin Oral 500 mg once daily" from FIG. 6.

Alternative Embodiments

Alternative embodiments of the system may comprise features that are, in some respects, similar to the various components described above. Selected distinguishing features of these alternative embodiments are discussed below.

Physician Order Format to Pharmacy Order Format Conversion

In particular embodiments, the system may be adapted to convert an order string in a physician order format to an order string in a pharmacy order format. In various embodiments, the system may convert the order string in physician order format by, after receiving the order string in physician order format at Step 210, retrieving information from a pharmacy database concerning the order string in the physician order format at Step 220. The system may then use the information retrieved at Step 220 to convert the order string to a second, pharmacy order format at Step 230 before displaying the order string in the pharmacy order format at Step 240. In particular embodiments, the conversion of an order string from a physician order format to a pharmacy order format may include making conversions that are substantially the opposite of conversions made when converting a pharmacy order format to a physician order format as described above.

Most Common Order Display Variations

In particular embodiments, the system may be adapted to determine the most commonly prescribed orders based at least in part on past order information associated with a particular health care professional. For example, the set of most commonly prescribed orders displayed for a particular surgeon may contain the most commonly prescribed orders that the surgeon has ordered herself. In other embodiments, the system may be adapted to determine the most commonly prescribed orders by practice area. For example, if a surgeon is using the system to make a new order, the system may display a set of most commonly prescribed orders based on the orders placed by all surgeons at a particular health care facility.

In other embodiments, the set of most commonly prescribed orders may not be limited to a particular health care facility. The set of most commonly prescribed orders may include, for example, the most commonly prescribed orders at all hospitals in the state of Georgia or all hospitals that are using the system.

In various embodiments, the system may display a most common set of orders at Step 130 that includes a mixture of the most common orders placed by a particular health care professional (e.g., a physician) in addition to the most common orders placed at the health care facility with which that physician is associated. In particular embodiments, the system may display the most common orders placed by a particular department of a particular health care facility. For example, the most common set of orders displayed to a physician working in the neo-natal department of a hospital may include a set of orders that includes the most common orders placed by all health care professionals in the neo-natal department.

Most Common Order Determination Methods

In particular embodiments, the system may determine, at Step 120, the most commonly prescribed orders by determining the most commonly prescribed orders for a particular calendar year. In various embodiments, the system may determine the most commonly prescribed orders over other suitable time frames (e.g., one month, five years, six months). In other embodiments, the system may determine the most commonly prescribed orders using all available past order information. In various embodiments, the system may be adapted to substantially continuously update the set of most common orders as new orders are placed.

Conclusion

Many modifications and other embodiments of the invention will come to mind to one skilled in the art to which this invention pertains having the benefit of the teachings presented in the foregoing descriptions and the associated drawings. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for the purposes of limitation.

We claim:

1. A non-transitory computer-readable medium storing computer-executable instructions for:

accessing, by a server including one or more processors, a plurality of data sources for pharmacy-formatted data, the pharmacy-formatted data representing a plurality of data elements, each data element of the plurality of data elements including a previous request communication received at a data source during a particular period of time, each request communication in the plurality of previous request communications including each of location data representing a location associated with the previous request communication and a combination specification that identifies, using a pharmacy-order format, each of a drug and a dosage of the drug;

processing, by the server, the plurality of previous request communications included in the pharmacy-formatted data, the processing including:

computing, by the one or more processors, for each combination specification included in the plurality of previous request communications, a number of other previous request communications that include the combination specification;

comparing, by the server, the number against a first threshold;

automatically determining, by the one or more processors, based at least in part on the pharmacy-formatted data, an order prevalence for each combination specification included in the plurality of previous request communications based on the comparing, the order prevalence of a combination specification representing a popularity of the combination specification;

identifying, by the one or more processors, based at least in part on the order prevalence for each combination specification included in the plurality of previous request communications, a set of prevalent combination specifications, each prevalent combination specification in the set of prevalent combination specifications identifying, using the pharmacy-order format, each of a drug and a dosage of the drug, the set of prevalent combination specifications representing commonly prescribed medications, and the set of prevalent combination specifications enabling a user device to select a combination specification from the commonly prescribed medications; and continuously updating the set of prevalent combination specifications as new request communications are received, a new request communication including a new combination specification, and continuously updating the set including incorporating the new combination specification into the set of prevalent combination specifications when a number of the new request communications associated with the new combination specification meets or exceeds a second threshold;

transmitting, by the one or more processors, a query communication to a pharmacy database, the query communication including a request for a subset of the set of prevalent combination specifications, the query communication requesting physician-formatted data for each of the set of prevalent combination specifications, the physician-formatted data being stored at the pharmacy database, and the physician-formatted data including transformation data for transforming a prevalent combination specification from a pharmacy order format to a physician order format;

determining the subset of the set of prevalent combination specifications, each prevalent combination specification of the subset corresponding to a defined location, the determination of the subset including a comparison between the location data associated with each prevalent combination specification and the defined location;

receiving, by the one or more processors, a query response from the pharmacy database, the query response including the physician-formatted data for each of the subset of prevalent combination specifications;

transforming, by the one or more processors, each of the subset of prevalent combination specifications from the pharmacy order format to the physician order format using the physician-formatted data, the transformation comprising at least one of transforming a brand name for a medication associated with the order into a generic name for the medication, transforming a dosing information into a total dosage, transforming a pharmacist delivery route code to a physician delivery route code, and transforming a pharmacist delivery time code to a physician delivery time code;

transmitting, to a mobile user device, an identification, in a physician order format, of a drug and a dosage of the drug as included in each of the transformed subset of prevalent combination specifications; and displaying, at the mobile user device, a representation of each of the subset of prevalent combination specifications in the physician order format; and receiving, from the mobile user device, input corresponding to a selection of a prevalent combination specification of the displayed subset of prevalent combination specifications.

2. The computer-readable medium of claim 1, wherein, for each of at least one of the transformed subset of prevalent combination specifications, the transformed subset of prevalent combination specification includes, in a prescribing physician order format, an identification of a route of administration for a drug entity, and wherein, for each of the at least one of the transformed subset of prevalent combination specifications, the identification of the drug and dosage of the drug is provided in association with an identification, in the prescribing physician order format, of the route of administration.

3. The computer-readable medium of claim 1, wherein the user device is operated by a physician.

4. The computer-readable medium of claim 1, wherein, for each of at least one of the transformed subset of prevalent combination specifications, the transformed subset of prevalent combination specification includes, in a prescribing physician order format, an identification of a number of doses of the drug to be taken by a patient, and wherein, for each of the at least one of the transformed subset of prevalent combination specifications, the identification of the drug and dosage of the drug is provided in association with an identification of the number of doses.

5. The computer-readable medium of claim 4, wherein:
when in the pharmacy order format, the selection of the prevalent combination specification specifies a particular pharmaceutical product that includes the drug of the selected prevalent combination specification.

6. The computer-readable medium of claim 5, wherein, when in the pharmacy order format, the selection of the prevalent combination specification specifies how much of the particular pharmaceutical product is to be provided to a patient at a particular time.

7. The computer-readable medium of claim 1, wherein converting data from each of the subset of prevalent combination specifications included past orders from the pharmacy order format to a prescribing physician order format comprises:
determining a particular drug entity that is included in a particular pharmaceutical product.

8. The computer-readable medium of claim 1, wherein accessing the information regarding the plurality of past orders comprises accessing the information from the pharmacy database.

9. The computer-readable medium of claim 1, wherein a health care facility is a hospital.

10. A non-transitory computer-readable medium storing computer-executable instructions for:
accessing a plurality of data sources for pharmacy-formatted data, the pharmacy-formatted data representing a plurality of data elements, each data element of the plurality of data elements including a previous request communication received at a data source during a particular period of time, each request communication in the plurality of previous request communications including each of location data representing a location associated with the previous request communication and a combination specification that identifies, using a pharmacy-order format, each of a drug and a dosage of the drug;
processing the plurality of previous request communications included in the pharmacy-formatted data, the processing including:
computing for each combination specification included in the plurality of previous request communications, a number of other previous request communications that include the combination specification;
comparing the number against a first threshold;
automatically determining based at least in part on the pharmacy-formatted data, an order prevalence for each combination specification included in the plurality of previous request communications based on the comparing, the order prevalence of a combination specification representing a popularity of the combination specification;
identifying based at least in part on the order prevalence for each combination specification included in the plurality of previous request communications, a set of prevalent combination specifications, each prevalent combination specification in the set of prevalent combination specifications identifying, using the pharmacy-order format, each of a drug and a dosage of the drug, the set of prevalent combination specifications representing commonly prescribed medications, and the set of prevalent combination specifications enabling a user device to select a combination specification from the commonly prescribed medications; and
continuously updating the set of prevalent combination specifications as new request communications are received, a new request communication including a new combination specification, and continuously updating the set including incorporating the new combination specification into the set of prevalent combination specifications when a number of the new request communications associated with the new combination specification meets or exceeds a second threshold;
transmitting a query communication to a pharmacy database, the query communication including a request for a subset of the set of prevalent combination specifications, the query communication requesting physician-formatted data for each of the set of prevalent combination specifications, the physician-formatted data being stored at the pharmacy database, and the physician-formatted data including transformation data for transforming a prevalent combination specification from a pharmacy order format to a physician order format;
determining the subset of the set of prevalent combination specifications, each prevalent combination specification of the subset corresponding to a defined location, the determination of the subset including a comparison between the location data associated with each prevalent combination specification and the defined location;
receiving a query response from the pharmacy database, the query response including the physician-formatted data for each of the subset of prevalent combination specifications;
transforming each of the subset of prevalent combination specifications from the pharmacy order format to the physician order format using the physician-formatted data, the transformation comprising at least one of transforming a brand name for a medication associated with the order into a generic name for the medication, transforming a dosing information into a total dosage, transforming a pharmacist delivery route code to a physician delivery route code, and transforming a pharmacist delivery time code to a physician delivery time code;
transmitting, to a mobile user device, an identification, in a physician order format, of a drug and a dosage of the drug as included in each of the transformed subset of prevalent combination specifications; and
displaying, at the mobile user device, a representation of each of the subset of prevalent combination specifications in the physician order format; and
receiving, from the mobile user device, input corresponding to a selection of a prevalent combination specification of the displayed subset of prevalent combination specifications.

11. The computer-readable medium of claim 10, wherein, for each of at least one of the transformed subset of prevalent combination specifications, the transformed subset of prevalent combination specification includes, in a prescribing physician order format, an identification of a route of administration for the drug entity, and wherein, for each of the at least one of the transformed subset of prevalent combination specifications, the identification of the drug and dosage of the drug is provided in association with an identification, in the prescribing physician order format, of the route of administration.

12. The computer-readable medium of claim 10, wherein the user device is operated by a physician.

13. The computer-readable medium of claim 10, wherein, for each of at least one of the transformed subset of prevalent combination specifications, the transformed subset of prevalent combination specification includes, in a prescribing physician order format, an identification of a number of doses of the drug to be taken by a patient, and wherein, for each of the at least one of the transformed subset of prevalent combination specifications, the identification of the drug and dosage of the drug is provided in association with an identification of the number of doses.

14. The computer-readable medium of claim 13, wherein:
when in the pharmacy order format, the selection of the prevalent combination specification specifies a particular pharmaceutical product that includes the drug of the selected prevalent combination specification.

15. The computer-readable medium of claim 14, wherein, when in the pharmacy order format, the selected prevalent combination specification specifies how much of the particular pharmaceutical product is to be provided to a patient at a particular time.

16. The computer-readable medium of claim 10, wherein converting data from each of the subset of prevalent combination specifications included past orders from the pharmacy order format to a prescribing physician order format comprises:
determining a particular drug entity that is included in a particular pharmaceutical product.

17. The computer-readable medium of claim 10, wherein accessing the information regarding the plurality of past orders comprises receiving the information from the pharmacy database.

18. The computer-readable medium of claim 10, wherein each individual in the set of individuals includes an individual associated with a same medical specialty.

19. The computer-readable medium of claim 18, wherein a medical facility is a hospital.

20. The computer-readable medium of claim 1, further comprising converting data from the selected the prevalent combination specification from a prescribing physician order format to a pharmacy order format.

* * * * *